United States Patent [19]

Suerken et al.

[11] Patent Number: 4,649,220

[45] Date of Patent: Mar. 10, 1987

[54] METHOD FOR PERFORMING ORGANIC REACTIONS IN SILICONE OILS

[75] Inventors: Hans P. Suerken, Zaltbommel, Netherlands; Jürgen Amort, Troisdorf-Sieglar; Horst Hanisch, Hennef, both of Fed. Rep. of Germany; Hendrikus van der Maas, Zuilichem, Netherlands

[73] Assignee: Dynamit Nobel AG, Cologne, Fed. Rep. of Germany

[21] Appl. No.: 759,920

[22] Filed: Jul. 26, 1985

Related U.S. Application Data

[63] Continuation of Ser. No. 561,164, Dec. 14, 1983, abandoned.

[30] Foreign Application Priority Data

Dec. 24, 1982 [DE] Fed. Rep. of Germany ....... 3247994
Mar. 8, 1983 [DE] Fed. Rep. of Germany ....... 3308089

[51] Int. Cl.$^4$ ...................... C07B 43/04; C07C 85/04
[52] U.S. Cl. .................................. 564/296; 546/312; 549/540; 556/450; 556/460; 556/461; 564/282
[58] Field of Search ....................... 556/450, 460, 461; 549/540; 564/296, 282; 546/312

[56] References Cited

U.S. PATENT DOCUMENTS 3,965,178 6/1976 Johnson ....................... 260/567.6 M
4,176,131 11/1979 Shih et al. ........................... 556/442
4,234,441 11/1980 Scott et al. ........................... 556/450

OTHER PUBLICATIONS

Kirk–Othmer, "Encyclopedia of Chemical Technology" Third Edition (1982), pp. 955–956.
Shih, et al., "Optionally Substituted Silicon Isocyanates," Chemical Abstracts 92:76,659s (1979).

*Primary Examiner*—Henry R. Jiles
*Assistant Examiner*—Dale A. Bjorkman
*Attorney, Agent, or Firm*—Felfe & Lynch

[57] ABSTRACT

Disclosed is a process for the performance of organic reactions in the liquid phase wherein silicone oils are used as the reaction medium. These silicone oils have no functional groups, are liquid at room temperature and have viscosities between 40 and 20,000 cs. at 25° C. The obtained reaction products are very pure and generally do not require additional purifying operations.

5 Claims, No Drawings

METHOD FOR PERFORMING ORGANIC REACTIONS IN SILICONE OILS

This application is a continuation of application Ser. No. 561,164, filed Dec. 14, 1983, abandoned.

BACKGROUND OF THE INVENTION

The present invention relates to the performing of organic reactions in certain reaction media.

It is generally known to perform organic reactions in organic solvents. The most important solvents are aliphatic or aromatic hydrocarbons or aliphatic or aromatic alcohols, a number of ketones, ethers, esters, and short-chain chlorinated hydrocarbons. The choice of a solvent as a reaction medium is determined by the solubility of the reactants in the solvents, and the solubility of the reaction product or products in the solvent. Also important in the selection of a solvent as a reaction medium are the volatility, combustibility and rate of evaporation of the solvent. Furthermore, in virtually all cases, the choice of a solvent as a reaction medium is governed by the extent to which the solvent reacts with the reactants or reaction products.

It is furthermore known that a great number of organic reactions in the above-named solvents result in unsatisfactory yields or in the formation of contaminated end products. The problem therefore existed of finding for the performance of organic reactions a reaction medium which has a good solvent power for the reactants or for a desired end product, in which the desired reactions can be performed such that secondary reactions do not take place or do so to a minor degree, and in which very pure end products are obtained. At the same time, the process to be performed in these desired solvents is to be as simple as possible and is not to involve a large investment in apparatus.

DESCRIPTION OF THE INVENTION

For the solution of this problem, a method has now been found for performing organic reactions in liquid reaction media, which is characterized in that the reactants are dissolved, suspended, dispersed or emulsified in a silicone oil. The reaction is then performed in the silicone oil, and the reaction products are then separated in a known manner.

The method of the invention is suitable for use, for example, in the reaction of amines with esters, alkoxy compounds or alkylhalides, as for example in condensation reactions or in the performance of substitution reactions, in which halogen hydride, especially hydrogen chloride, is liberated. The reaction of amines, especially tertiary amines, with alkyl halides leads to the formation of quaternary ammonium salts.

The reactants in this case are on the one hand alkyl halides in which the alkyl groups can be substituted by functional moieties which do not react with the siloxanes, and on the other hand either amines, alcohols or alcoholates, or mercaptans. Generally, the substitution reactions take place in accordance with the following equations:

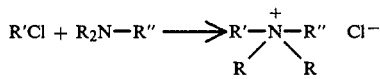

and

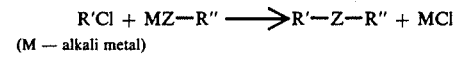

wherein R' represents alkyl or preferably 1 to 8 carbon atoms, or phenyl, R represents hydrogen or alkyl moieties of 1 to 4 carbon atoms, and R" can represent H or R' and Z can represent oxygen or sulfur. Bromine or iodine can replace the chlorine as halogen.

Instead of the alkyl halide, a chloroacetal can be made to react with an amine, preferably a secondary amine. The amine in this case is used in an excess in order to bind the hydrogen chloride that is being released.

In the preparation of compounds in accordance with these equations, the procedure performed in siloxanes has the advantage that products are obtained with great purity and in great yields. In the procedure practiced in the solvents used heretofore, the yields are lower, and the reaction products obtained are not in such pure form. Examples of compounds which can be made in this manner are oxirane methanamine-N,N,N-trimethyl chloride (also known by the name of glycidyl trimethylammonium chloride), tetrabutylammonium bromide, and benzyltriethylammonium bromide.

Also suitable starting compounds for the preparation of organic ammonium salts, however, are aromatic sulfonic acids and sulfonic acid chlorides which can be reacted with amines in accordance with the invention. The aromatic nucleus in that case can be substituted by alkyl groups or by halogen. Both the sulfonamic acids and the tertiary ammonium salts can be prepared. Here the method of the invention has the advantage that the desired reaction product is produced as a solid in the siloxane and thus can easily be separated from the rest of the reactants.

The reaction of amines with compounds containing alkoxy groups is performed preferably with compounds which contain a methoxy or ethoxy group in the alpha position in relation to an unsaturated group. Examples of starting compounds of this kind are methoxymethylenemalonic acid dimethyl ester and ethoxymethylene malonic acid diethyl ester.

In the reaction of amines with carboxylic acid esters, the carboxylic acid ester is preferably an aromatic ester, whose ester component has 1 to 4 carbon atoms. Ammonia can also be used as the amine in this case. Products which can be made in this manner are, for example, benzoic acid methylamide (from benzoic acid esters and monomethylamine) or toluyl amide from a toluyl ester and ammonia.

The method of the invention using siloxanes as reaction medium furthermore makes possible the performance of phase transition reactions, as described by J. Dockx, synthesis, 1973, page 441 in which the aqueous phase serves mainly as the second phase. The second phase, however, can also be another organic solvent that is not miscible with the siloxanes.

In the case in which one of the reactants is not soluble in the silicone oil, it can either be melted and dissolved in the molten state and added to the silicone oil, or it is dissolved in an organic solvent and added to the silicone oil. Then the organic solvent used can be distilled out.

The siloxanes that can be used in accordance with the invention are oligomers and polymers based on dimethylsiloxane, which may have either a ring structure or a chain structure. Branches are also possible. They must not enter any reaction with alkyl or aryl halides, and if possible they are to have no functional groups. Furthermore, they are to be liquid both at room temperature and, if possible, at temperatures up to about 200° C., preferably up to 100° C. The viscosity of the siloxanes that can be used, and which can also be called silicone oils, is between about 40 and about 20,000 centistokes, preferably between 50 and 2000 centistokes, at 25° C. Most of the compounds named hereinbelow satisfy these conditions.

The silicone oils that can be used include especially those compounds which contain as structural elements the grouping:

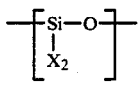

wherein X represents an alkyl group of 1 to 4 carbon atoms preferably the methyl group, or a phenyl moiety. Preferably, the alkyl group or the phenyl moiety are unsubstituted. Those compounds are used preferably in which one of the two moieties X is a phenyl moiety. Examples of compounds which come under this formula are hexamethyldisiloxane, hexaethyldisiloxane, hexakis(2-ethylbutoxy)disiloxane, 1,3-dimethyl-1,3-diphenyldisiloxane, 1,1,3,3-tetraphenyl-1,-3-dimethyldisiloxane, 1,1,5,5-tetraphenyl-1,3,3,5-tetramethyltrisiloxane, 1,1,3,5,5-pentaphenyl-1,3,5-trimethyltrisiloxane, polydimethylsiloxane, polydimethyldiphenylsiloxane, polymethylphenyldiphenyldisiloxane, and polydiphenylsiloxane. The terminal groups of the polymers are preferably trimethylsiloxy groups.

Examples of silicone oils having a ring structure are hexamethylcyclotrisiloxane, octamethylcyclotetrasiloxane, decamethylcyclopentasiloxane or hexaphenylcyclotrisiloxane.

Alkyl trialkoxysilanes whose ester groups are completely substituted by trialkylsilyl groups can also be used in accordance with the invention as reaction media. Such compounds and their preparation are described, for example, in German Pat. No. 2,642,833. Also, tetrakis(trialkylsiloxy) silanes, compounds which are known commercially by the name "Schweizerkreuz", can be used in accordance with the invention. These compounds can be conceived of as orthosilicic acid esters in which the alkyl moieties of the ester groups are replaced by trialkylsilyl groups.

EXAMPLE 1

94.9 of epichlorohydrin (=1.026 mol) is dissolved in 450 ml of hexamethyldisiloxane. 59 g (=1 mol) of trimethylamine is introduced into the solution through a gas introduction tube. At the end of an hour, the desired oxirane methylamine-N,N,N-trimethylchloride had precipitated as a solid; no elevation of temperature occurred, and throughout the reaction the temperature remained between 20° and 25° C.

At the end of 24 hours, the solid was filtered out on a closed filter, washed out with hexamethyldisiloxane and then vacuum-dried.

The epoxide content of the dried product was about 93 to 94%.

One mole of epichlorohydrin was added to the mother liquor, and again 59 g of trimethylamine was introduced. 24 hours later the precipitated end product was removed and worked up in the manner described above. The solid obtained again had a purity of 93 to 94%.

EXAMPLE 2

138.7 g of epichlorohydrin was dissolved or suspended in 378 g of a polydimethylsiloxane with a viscosity of 50 centistokes at 25° C. Then 59 g of trimethylamine was introduced. The epichlorohydrin dissolved completely in the polydimethylsiloxane as the trimethylamine was introduced, and after 20 minutes the first crystals of oxirane methylamine-N,N,N-trimethylchloride formed. At the end of 24 hours, the solid was filtered off and worked up as in Example 1, the first washing being performed with polydimethylsiloxane.

The mother liquor was treated in the same manner. Here, again, the first crystals formed at the end of 20 minutes. At the end of 24 hours, the precipitate was again filtered out and worked up as described above. It had a purity of 92 to 93%. The yield amounted to 55% with respect to the trimethylamine input.

The remaining mother liquor was processed in the same manner as the mother liquor of the first batch. It led to an end product of the same purity; the yield, with respect to trimethylamine, however, was 72%.

EXAMPLE 3

The procedure was the same as in Examples 1 and 2, but a polymethylphenylsiloxane was used as the silicone oil. The working up of the precipitate of the first reaction gave a yield of 37.4% with respect to trimethylamine with a purity of 93 to 95%. The working up of the mother liquor of this first reaction gave a yield of 92%, with respect to the trimethylamine input.

EXAMPLE 4

PREPARATION OF TETRABUTYLAMMONIUM BROMIDE

The preparation of this compound is described, for example in U.S. Pat. No. 3,965,178. In that case, the process is performed in acetonitrile as the solvent, and yields of more than 50% are obtained. The use of acrylonitrile, however, calls for a great deal of safety measures which make the process uneconomical. To obviate these disadvantages, it had already been proposed to perform the reaction in higher alcohols, esters or ketones. However, yields were obtained which were around only 50%, reaction times of about 48 hours having been required in some cases.

In accordance with the invention, 186 g (=1 mole) of tributylamine was dissolved in 1000 g of a polydimethylsiloxane having a viscosity of 50 centistokes. To this solution, 1 mole (=137 g) of butylbromide was added, which was lightly dyed. With slight refluxing at the beginning of the reaction, the mixture was allowed to react at 150° to 155° C. for 20 hours. Then the remaining vOlatile components were separated at reduced pressure.

The reaction mixture obtained was cooled and the crystalline mass was dissolved in water. The bottom solution of tetrabutylammonium bromide was separated and the dye was removed by washing with toluene. From the remaining aqueous solution it was possible by evaporation to obtain 234.5 g of a white, pure, end product, whose purity was 99.5 to 100%, with respect to bromine. The yield was 72.6%.

EXAMPLE 5

PREPARATION OF BENZYLTRIETHYLAMMONIUM CHLORIDE

In the manner described in Example 4, 101 g of triethylamine (1 mole) was dissolved in 200 g of polydimethylsiloxane. 137 g (1 mole) of benzyl chloride was stirred into this solution. After a reaction time of 5 hours at 80° C., a large amount of solid had formed, which was filtered out and washed with methyl ethyl ketone.

After drying, 174 g of benzyltriethylammonium chloride was obtained with a purity of 99.4 to 99.5%. The yield was about 76.3%.

EXAMPLE 6

Under nitrogen, 600 g of a methyl phenyl polysiloxane, which is commercially obtainable under the name Siliconoel PD-5 (manufactured by Bayer AG, Leverkusen), was mixed with 216.4 g (=1 mole) of ethoxymethylenemalonic acid diethyl ester and 108 g (=1 mole) of 6-methyl-2-aminopyridine. The aminopyridine was in the molten state, in which it was soluble in the silicone oil. The mixture was maintained at a reaction temperature between 90° and 100° C., and the alcohol that formed during the reaction was distilled out under a low vacuum. After the distillation of alcohol ended, the reaction medium was cooled to 60°.

In the cooled silicone oil, the desired methylpyridylaminomethylenemalonic acid diethyl ester was obtained in the form of crystals which were filtered out, washed at 20°, and dried. The yield of the product thus obtained, which had a purity of 99%, was 316 g =96.9%.

It will be understood that the specification and examples are illustrative but not limitative of the present invention and that other embodiments within the spirit and scope of the invention will suggest themselves to those skilled in the art.

We claim:

1. A process for the performance of reactions between alkyl halides and tertiary amines wherein the reaction is carried out in a silicone oil, the viscosity of which is from 40 to 20,000 centistokes at 25° C.

2. The process of claim 1, wherein the alkyl halide is a methyl halide.

3. The process of claim 1, wherein the silicone oil is selected from the group consisting of hexamethyldisiloxane, hexaethyldisiloxane, hexakis (2-ethylbutoxy)-disiloxane, 1,3-dimethyl-1,3-diphenyldisiloxane, 1,1,3,3-tetraphenyl-1-3-dimethyldisiloxane, 1,1,5,5,-tetraphenyl-1,3,3,5-tetramethyltrisiloxane, 1,1,3,5,5,-pentaphenyl-1,3,5-trimethyltrisiloxane, polydimethylsiloxane, polydimethyldiphenylsiloxane, polymethylphenyldiphenyldisiloxane, and polydiphenylsiloxane.

4. The process of claim 1, wherein the silicone oil is a silicic acid ester substituted by silyl groups.

5. the process of claim 1, wherein the separation of the reaction product or products is performed by means of a solvent which is not soluble in the silicone oil.

* * * * *